United States Patent [19]
McNeal

[11] Patent Number: 5,929,963
[45] Date of Patent: *Jul. 27, 1999

[54] CORRECTIVE LENS SYSTEM AND SUPPORT APPARATUS FOR USE WITH PROTECTIVE EYEWEAR DEVICES

[75] Inventor: Joseph R. McNeal, Hailey, Id.

[73] Assignee: Smith Sport Optic, Inc., Ketchum, Id.

[ * ] Notice: This patent issued on a continued prosecution application filed under 37 CFR 1.53(d), and is subject to the twenty year patent term provisions of 35 U.S.C. 154(a)(2).

[21] Appl. No.: 08/719,321

[22] Filed: Sep. 25, 1996

[51] Int. Cl.⁶ ........................................................ G02C 9/00
[52] U.S. Cl. .................................................. 351/47; 351/57
[58] Field of Search ............................... 351/47, 57, 158, 351/41, 43, 44, 137, 136

[56] References Cited

U.S. PATENT DOCUMENTS

| | | | |
|---|---|---|---|
| D. 339,364 | 9/1993 | Bollé | D16/123 |
| 3,051,957 | 9/1962 | Chan | 351/43 |
| 5,371,555 | 12/1994 | Nagel | 351/57 |
| 5,451,438 | 9/1995 | Bollé | 351/57 |
| 5,542,130 | 8/1996 | Grabos, Jr. et al. | 2/436 |
| 5,608,470 | 3/1997 | Sheffield | 351/57 |

*Primary Examiner*—Hung Xuan Dang
*Attorney, Agent, or Firm*—Seed & Berry LLP

[57] ABSTRACT

A corrective lens system and apparatus for use in protective eyewear devices such as ski goggles and sports shields is provided. In a preferred embodiment, a corrective lens assembly releasably snaps into place in multiple protective eyewear devices, allowing a user to own a single pair of corrective lenses for use with multiple devices. In preferred embodiments, the protective eyewear devices include a bridge support positioned behind the device lens for receiving and holding the corrective lens assembly. A nose clip embodiment is provided for use with ski goggles.

25 Claims, 2 Drawing Sheets

CORRECTIVE LENS SYSTEM AND SUPPORT APPARATUS FOR USE WITH PROTECTIVE EYEWEAR DEVICES

TECHNICAL FIELD

This invention relates to systems and apparatus for corrective lenses used in conjunction with goggles, sports shields, and other protective eyewear devices.

BACKGROUND OF THE INVENTION

Skiers, snowboarders, and motorcyclists commonly wear goggles to shield their eyes from sun, wind, and precipitation. Similar concerns by cyclists, in-line skaters, and others engaged in outdoor activities have led to the development and popularity of sports shields, a lighter weight athletic eyewear device typically having a polycarbonate lens which surrounds the eye region of the wearer's head to shield the eyes from sun and wind. Still other athletes wear sports goggles designed for activities such as basketball, soccer, and the like.

Athletic eyewear devices such as those described above offer various features and capabilities tailored to the types of activities for which they are designed. For individuals who enjoy multiple activities, it is not uncommon to own multiple protective eyewear devices corresponding to the different outdoor activities enjoyed by the individual.

While athletic eyewear devices have generally met the needs of users, they have not been entirely satisfactory for individuals who also must wear prescription lenses along with the protective eyewear. The shape and construction of the athletic eyewear devices typically make it impractical for the lenses of those devices to also provide correction for nearsightedness or farsightedness. Wearing a conventional pair of eyeglasses with corrective lenses along with an athletic eyewear device can be awkward or impractical. Attempts to offer custom arrangements for holding corrective lenses within goggles or sports shields have not been entirely satisfactory and, in any event, have required the owner of multiple pairs of protective eyewear to also own multiple pairs of specialized corrective lenses.

Athletic eyewear devices such as those described above are typically designed and intended to provide limited protection from the sun, wind and precipitation. As such, they do not provide protection from impacts as do specially designed safety goggles or similar devices. As used herein, the term "protective eyewear device" includes both athletic eyewear devices and eyewear devices designed to provide impact protection.

SUMMARY OF THE INVENTION

To overcome the deficiencies of the prior art, a corrective lens system for goggles, sports shields, and the like is provided. In a preferred system, multiple athletic eyewear devices are designed to receive a single corrective lens assembly. The corrective lens assembly includes a snap on bridge, with each athletic eyewear device including a bridge support for receiving and releasably holding the corrective lens assembly in the athletic eyewear device during use.

In accordance with a preferred embodiment of the present invention illustrated herein, goggles are fitted with a nose clip which hangs from the existing dual thermal lens structure to support a corrective lens assembly. The bridge portion of the corrective lens assembly snaps onto a bridge support on the lower region of the nose clip. The bridge and bridge support are shaped to provide a snap fit which will hold the corrective lens assembly in shape yet allow removal by the user for use in other protective eyewear devices.

In a sports shield preferred embodiment in accordance with the present invention, a corrective lens assembly as described above snaps in place behind the sports shield. The upper portion of the sports shield bridge is sized and shaped to receive and hold the corrective lens assembly bridge.

The bridge and bridge supports are preferably shaped to easily snap into place, yet remain in place during use. In preferred embodiments, a bridge with a central concave portion and convex regions on either side is provided, with the bridge forming a spring. The bridge supports are shaped to receive and hold the bridge and include recesses in some embodiments to receive and hold the convex regions on the bridge. Ascending lips on the bridge support block fore-and-aft movement of the bridge.

DETAILED DESCRIPTION OF THE INVENTION

As shown in the preferred embodiments illustrated and described herein, the present invention provides a corrective lens system for goggles, sports shields, and other protective eyewear devices. A lightweight protective lens assembly 10 is provided which can be easily and securely snapped in place for use within, for example, ski goggles 20 or a sports shield product 80. As such, the present invention provides a user with a useful, efficient and attractive corrective lens arrangement for use in conjunction with athletic eyewear devices such as goggles or sports shields. Also, significantly, the user need not purchase multiple corrective lens devices for the various athletic eyewear devices used in different types of athletic and outdoor activity—a single corrective lens assembly releasably mounts in different types of athletic eyewear devices.

The ability to use a single corrective lens assembly in multiple athletic eyewear devices offers considerable cost savings to users given the expense of corrective lenses. This is especially apparent in the case of users whose corrective lens prescription may change frequently. Another advantage of the preferred embodiments of the present system is that the athletic eyewear devices are fully functional when the corrective lens assembly is removed. This permits the athletic eyewear to be shared by different persons and permits individual users to wear both corrective eyeglasses and contact lens with the athletic eyewear devices.

Figure 1:
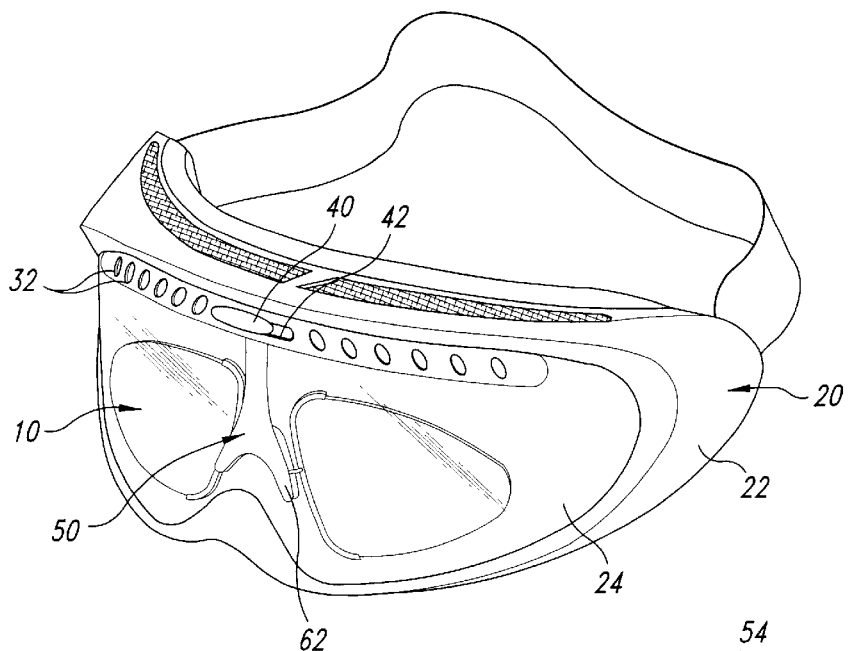
FIG. 1 is a perspective view of a preferred embodiment of the present invention, illustrating the front of a pair of goggles including a corrective lens assembly mounted to a nose clip.
Figure 2:
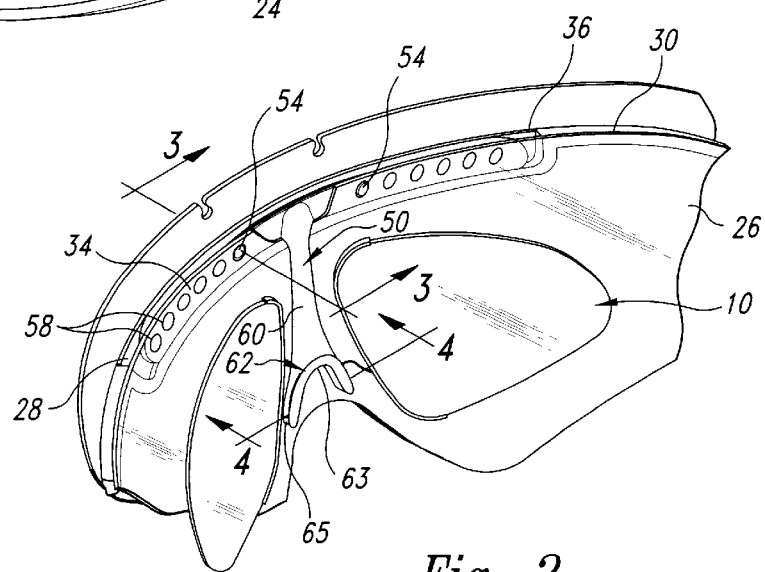
FIG. 2 is a cut-away, perspective view of the preferred embodiment of FIG. 1, looking forward from the back side of the corrective lens assembly and goggle lens structure.

FIGS. 1–4 illustrate a pair of goggles 20 for use by skiers or snowboarders, for example, comprising a preferred embodiment of the present invention. The ski goggle portion of the embodiment of FIG. 1 is of standard construction. A frame 22 holds a goggle lens structure 24 comprised of an inner lens 26 and an outer lens 28 separated by a closed-cell foam spacer 30. Ventilating holes 32, 58 extend through the outer lens 28 and inner lens 26 permitting fresh air to enter the region between the user's face (not shown) and the inner lens 26. As best seen in FIG. 2, a vent slide 34 resides in a slot 36 formed between the inner lens 26, the outer lens 28, and the foam spacer 30. The vent slide 34 and the slot 36 are sized to permit the vent slide 34 to move left to right, allowing the user of the goggles to align holes 38 in the vent slide 34 with respect to the holes 32 in the outer lens 28 and holes 58 in the inner lens 26, thereby regulating the flow of air through the goggles 20. The vent slide 34 includes a slide handle 40 extending forwardly from the central portion of the vent slide and extends through an elongated aperture 42 in the outer lens 28 to permit the user to grab the slide handle 40 while wearing the goggles and easily move the vent slide left to right.

Although the present invention can be implemented in connection with various types of conventional ski goggles, the preferred embodiment illustrated herein is adapted from a V3 Regulator™ Model V34LCH goggle available from Smith Sports Optics Incorporated of Ketchum, Id., the assignee of the present invention. It will be appreciated, then, that various design aspects of the goggles described herein, including for example the adjustable ventilating system which is also the subject of U.S. Pat. No. 5,542,130, need not be implemented to practice the present invention.

Figure 3:
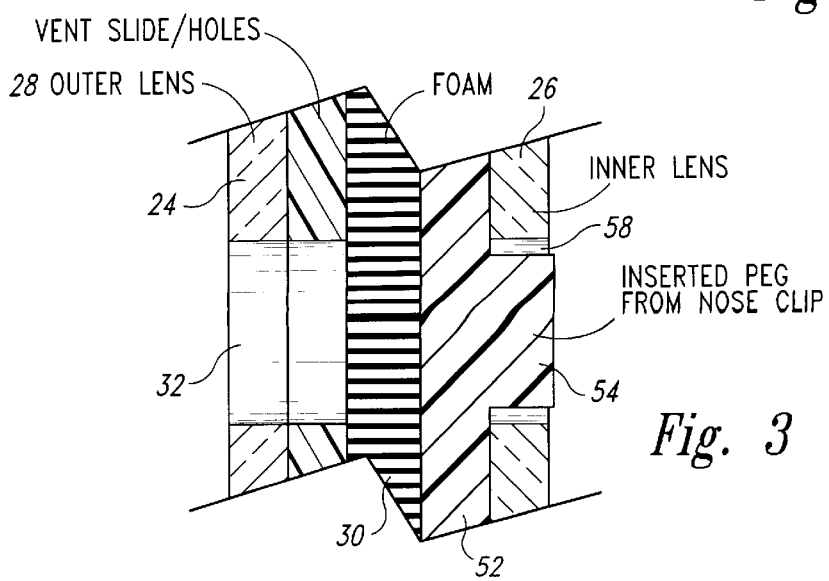
FIG. 3 is a cross-sectional view taken through line 3—3 of FIG. 2.

The improvements of the present invention are obtained in the embodiment illustrated in FIGS. 1 through 4 by the provision of a corrective lens assembly 10 which is releasably mounted on a nose clip 50 which has in turn been mounted to conventional ski goggles such as those described above. The nose clip includes an upper hanger portion 52 which is mounted over the top edge of the inner lens 26 as shown in FIGS. 2 and 3. The hanger portion 52 includes a hook portion 56 which, when installed in the goggles 20, projects forwardly over the inner lens 26 and downwardly below the ventilating holes 58. Pegs 54 project rearwardly from the back face of the hook portion 56 and are received within ventilating holes 58 in the upper portion of the inner lens 26 to secure the nose clip 50 to the goggles.

In the preferred embodiment of FIGS. 1–4, the inner lens 26 of goggles 20 has existing ventilating holes 58. For nose clips 50 designed for use with goggles having existing holes, the pegs 54 are preferably spaced apart and sized to fit snugly within the existing holes. For other types of goggles, appropriately sized and spaced holes may be added to the inner lens or alternate securing means may be employed.

The nose clip 50 extends downwardly from the hanger 52 via a support arm 60 which is sized to minimize interference with the user's vision and to place the corrective lens assembly 10 at an appropriate height with respect to the user's eyes. The bottom portion of the nose clip comprises a bridge support 62, preferably formed integrally with the support arm 60, for receiving and releasably mounting the corrective lens assembly 10. As seen in FIG. 2, the bridge support includes a rear lip 63 which raises upwardly to block rearward movement of the bridge 70 of the corrective lens assembly 10 (described in more detail below). A front lip 65 is integrally formed with the lower portion of the nose clip 50 support arm 60 to similarly block forward movement of the corrective lens assembly 10.

The nose clip assembly in the preferred embodiment illustrated herein is fabricated of clear propionate plastic, although other alternative materials can be used.

The corrective lens assembly 10 is comprised of a pair of corrective lenses 64, each of which is mounted to a metal frame piece 66 in a manner known in the art. For example, the frame pieces 66 may be configured to hold the lenses in place alone (not shown), by placing a connector through the lens (not shown), or for example, with the aid of conventional nylon cords 68 or the like which extend from the frame pieces 66 around the corrective lenses 64 to secure the corrective lenses with respect to the frames in a manner known in the art. The frame pieces 66 may be constructed of any suitable material as is known in the art. The frame pieces shown here are fabricated of optical grade stainless steel.

The corrective lenses 64 are of conventional construction and may be of various shapes. The shape used in the preferred embodiments illustrated herein was selected because it is believed to work well and present an attractive appearance with the corresponding ski goggles 20 and sports shield 80 embodiments illustrated herein. Alternative shapes can be used in these or other embodiments. Indeed, where a user's prescription dictates relatively thick corrective lenses 64, it may be desirable to use smaller lenses to yield a lighter weight corrective lens assembly 50 and avoid distortion which can occur when looking through the outer portions of larger, thicker lenses.

Figure 4:
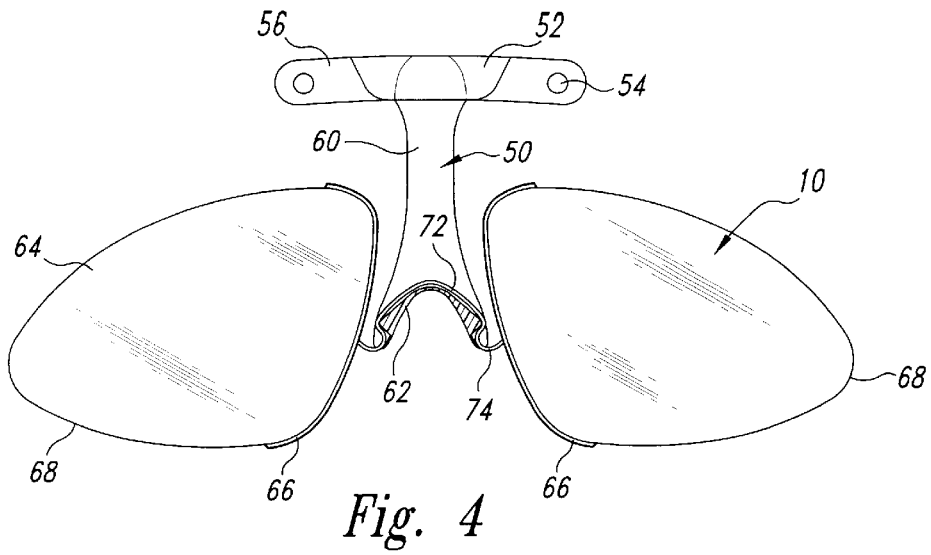
FIG. 4 is a cross-sectional view taken through line 4—4 of FIG. 2.

The frame pieces 66 holding the corrective lenses 64 are joined by a bridge 70. The bridge 70 in the preferred embodiments illustrated herein includes a central region 72 which is generally concave as viewed from the underside (as worn by a user) of the goggles 20, as best shown in FIG. 4. As the bridge extends outwardly from the central region 72 toward the frame pieces 66, there is a convex region 74 on each side proximate the corresponding frame piece 66. In combination, the concave central region 72 and convex regions 74 provide a configuration that enables the corrective lens assembly to be snapped in place over a correspondingly shaped region of the bridge support 62. The bridge 70 is preferably fabricated of lightweight metal and shaped to form a spring, such that in operation the convex regions 74 are biased inwardly to thereby assist in holding the bridge 70 on the bridge support 62. In the preferred embodiment illustrated herein, the bridge is fabricated of optical grade stainless steel. The shape of the bridge 70 permits the weight of the corrective lens assembly 10 to be supported by the bridge support 62 and to restrain lateral movement of the corrective lens assembly 10 with respect to the nose clip 50.

It will be appreciated that in certain situations it may be desirable to provide a means for wearing the corrective lens assembly 10 without wearing a protective eyewear device such as the ski goggles 70. For example, a user may desire to remove ski goggles during a lunch break, yet continue to wear the corrective lens 64. It will be appreciated that various conventional eyeglass frame technologies could be adapted to meet this need. For example, conventional frames (not shown) could be adapted to include a nose clip 50 as described herein to hold the corrective lens assembly 10. Alternately, a half-frame (not shown) such as is used for reading glasses could be fitted with a nosepiece 88 of the type described below including a bridge support 90 for holding the corrective lens assembly 10.

Figure 5:
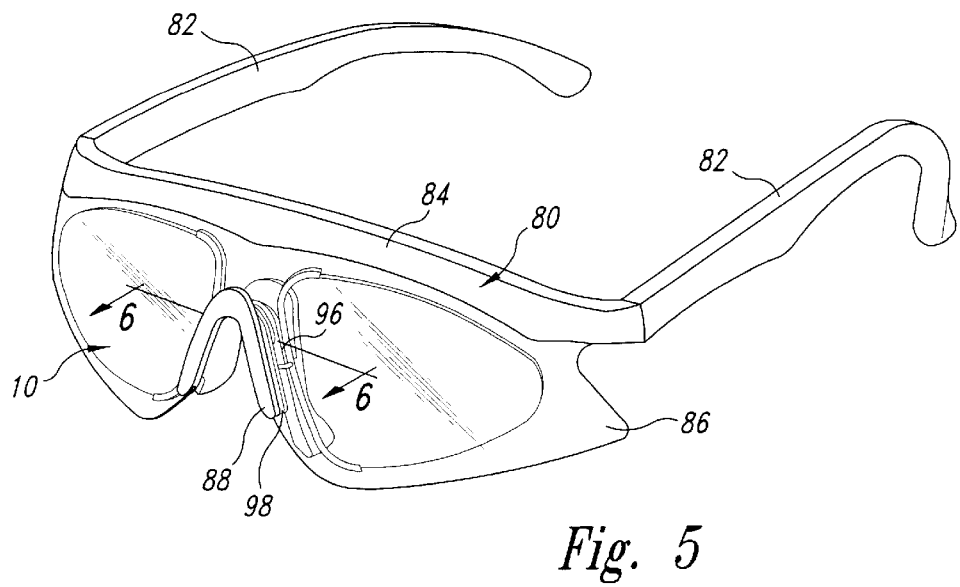
FIG. 5 is a perspective view of a preferred embodiment of the present invention, illustrating a front view of a sports shield device fitted with a corrective lens assembly in accordance with the present invention.
Figure 6:
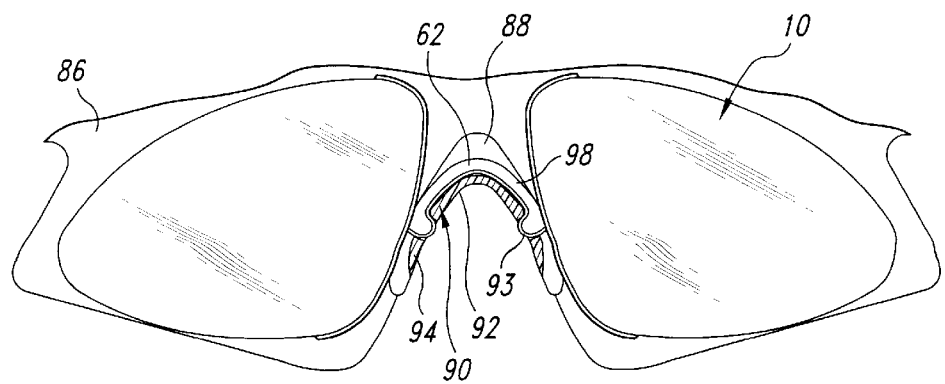
FIG. 6 is a cross-sectional view taken through line 6—6 of FIG. 5.

FIGS. 5 and 6 illustrate a preferred embodiment of the present invention comprising a sports shield device 80 to be worn by users for bicycling, in-line skating, or other comparable outdoor activities. The system and apparatus of the current invention can be implemented with various conventional sports shield devices and comparable products. The embodiment illustrated in FIGS. 5 and 6 has been adapted from a conventional MOAB® II sports shield product, Model No. MB3NBBHP, available from Smith Sport Optics Incorporated, of Ketchum, Id., assignee of the present invention. Side pieces 82 extend forwardly over a user's ears to support a central frame member 84. Depending from the central frame member 84 is a polycarbonate lens 86 designed to shield the user from sun and wind. A nosepiece 88 is mounted to the bottom of the central portion of the lens 86, as shown in FIG. 5, to permit the user's nose (not shown) to support the sports shield 80 during use.

As best seen in FIG. 6, the rear portion of the nosepiece 88, positioned behind the lens, includes a bridge support 90 shaped to receive and securely, releasably mount the bridge 62 of the corrective lens assembly. This arrangement is advantageous because it allows easy mounting and removal of the corrective lens assembly 10 within the sports shield product 80. Further, when the corrective lens assembly is removed, the sports shield product 80 remains fully functional, and thus can be used by the original wearer with contact lenses, for example, or by another person without any corrective lens.

In particular, the bridge support 90 of the preferred embodiment of FIGS. 5 and 6 includes an upper region 92 which supports the central region 72 of the bridge and a lower portion 94 which is positioned below the convex portion 74 of the bridge 62 to provide vertical support an additional securing therefore when the central region 72 is mounted within the nosepiece 88. The upper region 92 and portion 94 on each side of the bridge support 90 define recess portions 93 which receives the corresponding convex portion 74 of the bridge 62. The bridge support 90 of the nosepiece 88 also includes a rear lip 96 and a front lip 98 which extend upwardly on the front and back sides of the bridge support 90 to restrict rearward and forward movement of the bridge 70 of the corrective lens assembly 10, as seen in FIGS. 5 and 6.

Although the system and apparatus of the present invention have been described with respect to the preferred embodiments illustrated and described herein, the invention is not intended to be limited to or by these embodiments, but rather is defined by the claims which follow. It will be appreciated by those of skill in the art that the invention can be implemented in various embodiments. Further, although the invention has been described with respect to ski goggles and sports shield embodiments, it will be appreciated that the invention can be implemented with respect to various athletic and other protective eyewear devices.

I claim:

1. A corrective lens system for protective eyewear devices, comprising:
   a. a corrective lens assembly comprising:
      i. a pair of corrective lenses positioned in a generally co-planar relationship and spaced apart left to right along a perpendicular axis for viewing through a wearer's left and right eyes, respectively;
      ii. a frame attached to each of the corrective lenses for holding it in place;
      iii. a bridge attached to the frames and extending along the perpendicular axis between the corrective lens; and
   b. a first protective eyewear device designed for use in connection with a first activity comprising:
      i. a protective lens;
      ii. means for mounting the protective lens forward of a wearer's head; and
      iii. a bridge support mounted to the protective eyewear device and positioned behind the protective lens, the bridge support shaped to receive and releasably hold the bridge; and
   c. a second protective eyewear device, separate and distinct from the first protective eyewear device, designed for use in connection with a second activity different than the first activity, comprising:
      i. a protective lens;
      ii. means, separate from the first protective eyewear device mounting means, for mounting the protective lens forward of a wearer's head; and
      iii. a bridge support, separate from the first protective eyewear device bridge support, mounted to the protective eyewear device and positioned behind the protective lens, the bridge support shaped to receive and releasably hold the bridge.

2. The system of claim 1 wherein the bridge includes a curved central portion which is concave when viewed from below and wherein the bridge supports of the first and second protective eyewear devices include a correspondingly sized and shaped concave region for receiving the bridge.

3. The system of claim 2 wherein the bridge additionally includes a convex region to the left and right of the concave central portion.

4. The system of claim 3 wherein the bridge support of the first protective eyewear device includes a recess portion on the left and right sides thereof, the recessed portions extending inwardly, the recess portions positioned to receive the convex regions of the bridge and restrain vertical movement of the bridge when it is held within the protective eyewear device.

5. The system of claim 1 wherein the bridge supports of the first protective eyewear device includes a front lip portion and rear lip portion which raise up from the bridge support at locations in front of and behind the bridge, respectively, to block fore-and-aft movement of the bridge when it is mounted within the first protective eyewear device.

6. The system of claim 1 wherein the first protective eyewear device comprises a pair of ski goggles and the second protective eyewear device comprises a pair of sports shields.

7. Protective goggles comprising:
   a. a protective lens for shielding the wearer of the goggles from wind, precipitation, the protective lens including an upper portion positioned above the wearer's eyes;
   b. a main body portion holding the protective lens in front of the wearer's eyes during use; and
   c. an elongated nose clip depending from a location adjacent the upper region of the protective lens adjacent the back side of the protective lens to a location proximate the wearer's eyes, the nose clip including means for releasably mounting corrective lenses, wherein the nose clip further comprises a hanger on the upper portion thereof, the hanger extending forwardly and downwardly from the top of the nose clip to hang over the top of the protective lens.

8. The goggles of claim 7 wherein:
   d. the protective lens further includes a plurality of ventilating holes spaced apart across the top portion of the lens; and
   e. the nose clip hanger including at least one peg extending rearwardly from the back side of the hanger, each peg sized and positioned to extend through a ventilating hole in the protective lens.

9. The goggles of claim 7 wherein the mounting means comprises a bridge support positioned at the lower end of the nose clip for receiving the bridge of a corrective lens assembly.

10. The goggles of claim 9 wherein the bridge support further includes a lip rising upwardly from the bridge support to block fore-and-aft movement of a bridge mounted on the bridge support.

11. The goggles of claim 9 wherein the bridge support includes a curved central portion which is concave when viewed from below for receiving a correspondingly shaped bridge.

12. The goggles of claim 11 wherein the bridge support additionally includes recessed portions on either side of the central concave region for receiving projecting portions of a bridge.

13. An elongated nose clip for releasably mounting corrective lens within a pair of ski goggles, comprising:
 a. an upper portion for attaching to the goggles;
 b. a main body portion depending from the upper portion; and
 c. a bottom portion including means for releasably mounting corrective lenses to the goggles.

14. The nose clip of claim 13 wherein the mounting means comprises a bridge support for receiving the bridge portion of a corrective lens assembly.

15. The nose clip of claim 14 wherein the bridge support further includes a lip rising upwardly from the bridge support to block fore-and-aft movement of a bridge mounted on the bridge support.

16. The nose clip of claim 14 wherein the bridge support includes a curved central portion which is concave when viewed from below for receiving a correspondingly shaped bridge.

17. The nose clip of claim 14 wherein the bridge support additionally includes recessed portions on either side of the central concave region for receiving projecting portions of a bridge.

18. The nose clip of claim 13, further comprising:
 d. a hanger on the upper portion thereof, the hanger extending forwardly and downwardly from the top of the nose clip to hang over the top of the lens of the goggles.

19. The nose clip of claim 13 adapted for mounting on goggles having a protective lens with a plurality of ventilating holes spaced apart across the top portion of the lens, the upper portion of the nose clip further including:
 d. a hanger extending forwardly and downwardly from the upper portion of the nose clip to permit the nose clip to be hung over the protective lens, the hanger including at least one peg extending rearwardly from the back side of the hanger, each peg sized and positioned to extend through a ventilating hole in the protective lens.

20. The nose clip of claim 13, further including a pair of corrective lenses for releasably mounting to the nose clip.

21. A protective eyewear device comprising:
 a protective lens for shielding the wearer of the device from wind, precipitation;
 a frame portion mounted to the protective lens, the frame including left and right frame members extending rearwardly from the lens to support the device on the wearer's head; and
 a nosepiece attached to the bottom of the protective lens, the nosepiece shaped to rest on the wearer's nose and thereby support the protective eyewear device, the nosepiece extending behind the protective lens and including means positioned behind a corrective lens for releasably mounting corrective lens and wherein the mounting means comprises a bridge support for receiving the bridge of a corrective lens assembly, wherein the bridge support includes a lip rising upwardly from the bridge support to block fore-and-aft movement of a bridge mounted on the bridge support and a curved central portion which is concave when viewed from below for receiving a correspondingly shaped bridge, the bridge support additionally including recessed portions on either side of the central concave portion for receiving projecting portions of a bridge.

22. The protective eyewear device of claim 21 wherein the bridge support further includes a lip rising upwardly from the bridge support to block fore-and-aft movement of a bridge mounted on the bridge support.

23. The protective eyewear device of claim 21, further including a pair of corrective lenses for releasably mounting to the nose clip.

24. A corrective lens assembly for use in conjunction with a protective eyewear device, the corrective lens assembly comprising:
 a. a pair of corrective lenses spaced apart for viewing through a wearer's left and right eyes, respectively;
 b. a frame attached to each of the corrective lenses for holding it in place; and
 c. a bridge extending between the portions of the frame holding each corrective lens; the bridge includes a central portion which is concave when viewed from below and a convex portion positioned to the left and right of the concave portion.

25. The corrective lens assembly of claim 24, further including means for supporting the corrective assembly on a wearer's head when a protective eyewear device is not being worn.

* * * * *